United States Patent [19]
Kornberg et al.

[11] Patent Number: 6,096,744
[45] Date of Patent: *Aug. 1, 2000

[54] SULFONAMIDE DERIVATIVES OF SUBSTITUTED QUINOXALINE 2,3-DIONES AS GLUTAMATE RECEPTOR ANTAGONISTS

[75] Inventors: Brian Edward Kornberg; Sham Shridhar Nikam, both of Ann Arbor, Mich.

[73] Assignee: Warner-Lambert Company, Morris Plains, N.J.

[*] Notice: This patent issued on a continued prosecution application filed under 37 CFR 1.53(d), and is subject to the twenty year patent term provisions of 35 U.S.C. 154(a)(2).

[21] Appl. No.: 09/072,117

[22] Filed: May 4, 1998

Related U.S. Application Data

[60] Provisional application No. 60/059,723, Sep. 22, 1997.

[51] Int. Cl.$^7$ ...................... A61K 31/498; C07D 241/44
[52] U.S. Cl. ............................................ 514/249; 544/354
[58] Field of Search ..................................... 544/354, 337; 514/249, 85

[56] References Cited

FOREIGN PATENT DOCUMENTS

| | | |
|---|---|---|
| 0488959 | 6/1992 | European Pat. Off. . |
| 9308188 | 4/1993 | WIPO . |
| 9426747 | 11/1994 | WIPO . |
| 0627434 | 12/1994 | WIPO . |
| 97/08155 | 3/1997 | WIPO . |

OTHER PUBLICATIONS

Copending U.S. application No. 08/443507, 1995.

C.F. Bigge, and T.C. Malone, "Agonists, Antagonists and Modulators of the N–methyl–D–aspartic acid (NMDA) and α–amino–3–hydroxy–5–methyl–4–isoxazolepropanoic acid (AMPA) Subtypes of Glutamate Receptors", *Current Opinion in Therapeutic Patents*, 1993, pp. 951–989.

M. Rogawski, "Therapeutic potential of excitatory amino acid antagonists: channel blockers and 2,3–benzodiazepines", *TiPS*, vol. 14, 1993, pp. 325–331.

H. Li and A.M. Buchan, "Treatment with an AMPA Antagonists 12 Hours Following Severe Normothermic Forebrain Ischemia Prevents $CA_1$ Neuronal Injury", *Journal of Cerebral Blood Flow and Metabolism*, vol. 13, No. 6, 1993, pp. 933–939.

B. Nellgård and T. Wieloch, "Postischemic Blockade of AMPA but not NMDA Receptors Mitigates Neuronal Damage in the Rat Brain Following Transient Severe Cerebral Ischemia", *Journal of Cerebral Blood Flow and Metabolism*, vol. 12, No. 1, 1992, pp. 2–11.

R. Bullock et al., "Neuroprotective Effect of the AMPA Receptor Antagonist LY–293558 in Focal Cerebral Ischemia", *Journal of Cerebral Blood Flow and Metabolism*, vol. 14, No. 3, 1994, pp. 466–471.

D. Xue et al., "Delayed Treatment with AMPA, but Not NMDA, Antagonists Reduced Neocortical Infarction", *Journal of Cerebral Blood Flow and Metabolism*, vol. 14, No. 2, 1994, pp. 251–261.

X.–J. Xu et al., "Systemic Excitatory Amino Acid Receptor Antagonists of the α–amino–3–hydroxy–5–methyl–4–isoxazolepropnionic acid (AMPA) Receptor and of the N–methyl–D–aspartate (NMDA) Receptor Relieve Mechanical Hypersensitivity After Transient Spinal Cord Ischemia in Rats", *The Journal of Pharmacology and Experimental Therapeutics*, vol. 267, No. 1, 1993, pp. 140–144.

T. Namba et al., "Antiepileptic and anticonvulsant effects of NBQX, a selective AMPA receptor antagonists, in the rat kindling model of epilepsy", *Brain Research*, vol. 638, 1994, pp. 36–44.

S.E. Browne and J. McCulloch, "AMPA receptor antagonists and local cerebral glucose utilization in the rat", *Brain Research*, vol. 641, 1994, pp. 10–20.

S. Yamaguchi et al., "Anticonvulsant activity of AMPA/kainate antagonists: comparison of GYKI 52466 and NBQX in maximal electroshock and chemoconvulsant seizure models", *Epilepsy Research*, vol. 15, 1993, pp. 179–184.

S. Smith et al., "The non–N–methyl–D–aspartate receptor antagonists, BYKI 52466 and NBQX are anticonvulsant in two animal models of reflex epilepsy", *European Journal of Pharmacology*, vol. 201, 1991, pp. 179–183.

T. Klockgether et al., "The AMPA Receptor Antagonists NMQX Has Antiparkinsonian Effects in Monoamine–depleted Rats and MPTP–treated Monkeys", *Annals of Neurology*, vol. 30, No. 5, 1991, pp. 717–723.

T. Klockgether and L. Turski, "Toward an Understanding of the Role of Glutamate in Experimental Parkinsonism: Agonists–Sensitive Sites in the Basal Ganglia", *Annals of Neurology*, vol. 34, No. 4, 1993, pp. 585–593.

P. Francis et al., "Cortical Pyramidal Neurone Loss May Cause Glutamatergic Hypoactivity and Cognitive Impairment in Alzheimer's Disease: Investigative and Therapeutic Perspectives", *Journal of Neurochemistry*, vol. 60, No. 5, 1993, pp. 1589–1604.

S. Lipton, "Prospects for clinically tolerated NMDA antagonists: open–channel blockers and alternative redox states of nitric oxide", *TINS*, vol. 16, No. 12, 1993, pp. 527–532.

(List continued on next page.)

*Primary Examiner*—Emily Bernhardt
*Attorney, Agent, or Firm*—Elizabeth M. Anderson

[57] ABSTRACT

A novel series of substituted quinoxaline 2,3-diones useful as neuroprotective agents are taught. Novel intermediates, processes of preparation, and pharmaceutical compositions containing the compounds are also taught. The compounds are glutamate antagonists and are useful in the treatment of stroke, cerebral ischemia, or cerebral infarction resulting from thromboembolic or hemorrhagic stroke, cerebral vasospasms, hypoglycemia, cardiac arrest, status epilepticus, perinatal asphyxia, anoxia, seizure disorders, pain, Alzheimer's, Parkinson's, and Huntington's Diseases.

3 Claims, No Drawings

OTHER PUBLICATIONS

S. Lipton and P. Rosenberg, "Excitatory Amino Acids as a Final Common Pathway for Neurologic Disorders", Review Article in *Mechanisms of Disease*, F. Epstein, Editor, vol. 380, No. 9, 1993, pp. 613–622.

C. Bigge, "Structural Requirements for the Development of Potent N–methyl–D–aspartic Acid (NMDA) Receptor Antagonists", *Biochemical Pharmacology*, vol. 45, No. 8, 1993, pp. 1547–1561.

T. Honoré and M. Nielsen, "Complex Structure of Quisqualae–Sensitive Glutamate Receptors in Rat Cortex", *Neuroscience Letters*, vol. 54, 1985, pp. 27–32.

E. London and J. Coyle, "Specific Binding of [$^3$H]Kainic Acid to Receptor Sites in Rat Brain", *Molecular Pharmacology*, vol. 15, 1979, pp. 492–505.

S. Jones et al., "Characterization of the Binding of Radioligands to the N–Methyl–D–Aspartate, Phencyclidine, and Glycine Receptors in Buffy Coat Membranes", *Journal of Pharmacological Methods*, vol. 21, 1989, pp. 161–168.

J.–Y. Koh et al., "Non–NMDA Receptor–Mediated Neurotoxicity in Cortical Culture", *Journal of Neuroscience*, vol. 10, No. 2, 1990, pp. 693–705.

R. Kall et al., "Antiepileptic Drug Development: II. Anticonvulsant Drug Screening", *Epilepsia*, vol. 19, 1978, pp. 409–428.

Abstract for JP 06228112 (Aug. 16, 1994), Yamanouchi Pharm.

Acklin et al, *Chemical Abstracts*, vol. 126, No. 251169 (Abstract for WO 9708155, Mar. 6, 1997) (1997).

SULFONAMIDE DERIVATIVES OF SUBSTITUTED QUINOXALINE 2,3-DIONES AS GLUTAMATE RECEPTOR ANTAGONISTS

This application claims the benefit of U.S. Provisional Application Number 60/059,723 filed Sep. 22, 1997.

BACKGROUND OF THE INVENTION

The present invention concerns novel sulfonamide derivatives of substituted quinoxaline 2,3-diones having utility as glutamate receptor antagonists. The fused ring quinoxaline 2,3-dione system is substituted at the a- or b-position by sulfonamide derivatives. The compounds are active as excitatory amino acid receptor antagonists acting at glutamate receptors, including either or both N-methyl-D-aspartate (NMDA) receptors and non-NMDA receptors such as the α-amino-3-hydroxy-5-methyl-4-isoxazole propionic acid (AMPA) receptor and the kainate receptor. The invention also relates, therefore, to the use of those quinoxaline-2,3-diones as neuroprotective agents for treating conditions such as cerebral ischemia or cerebral infarction resulting from a range of phenomena, such as thromboembolic or hemorrhagic stroke, cerebral vasospasms, hypoglycemia, cardiac arrest, status epilepticus, perinatal asphyxia, anoxia such as from drowning, pulmonary surgery, and cerebral trauma, as well as to treat chronic neurodegenerative disorders such as Alzheimer's Disease, Parkinsonism, and Huntington's Disease, and seizure disorders and pain. The compounds of the present invention may also be useful in the treatment of schizophrenia, epilepsy, anxiety, pain, and drug addiction.

Excessive excitation by neurotransmitters can cause the degeneration and death of neurons. It is believed that this degeneration is in part mediated by the excitotoxic actions of the excitatory amino acids (EAA) glutamate and aspartate at the NMDA receptor, the AMPA receptor, and the kainate receptor. AMPA/kainate receptors may be referred to jointly as non-NMDA receptors. This excitotoxic action is considered responsible for the loss of neurons in cerebrovascular disorders such as cerebral ischemia or cerebral infarction resulting from a range of conditions, such as thromboembolic or hemorrhagic stroke, cerebral vasospasm, hypoglycemia, cardiac arrest, status epilepticus, perinatal asphyxia, anoxia such as from drowning, pulmonary surgery, and cerebral trauma, as well as lathyrism, Alzheimer's Disease, Parkinson's Disease, and Huntington's Disease.

Several classes of quinoxalinedione derivatives have been disclosed as glutamate (EAA) receptor antagonists. For example, among excitatory amino acid receptor antagonists recognized for usefulness in the treatment of disorders are those that block AMPA receptors (Bigge C. F. and Malone T. C., Curr. Opin. Ther. Pat., 1993:951; Rogawski M. A., TiPS, 1993;14:325). AMPA receptor antagonists have prevented neuronal injury in several models of global cerebral ischemia (Li H. and Buchan A. M., J. Cerebr. Blood Flow Metab., 1993;13:933; Nellgård B. and Wieloch T., J. Cerebr. Blood Flow Metab., 1992;12:2) and focal cerebral ischemia (Bullock R., Graham D. I., Swanson S., and McCulloch J., J. Cerebr. Blood Flow Metab., 1994;14:466; Xue D., Huang Z.-G., Barnes K., Lesiuk H. J., Smith K. E., and Buchan A. M., J. Cerebr. Blood Flow Metab., 1994;14:251). AMPA antagonists have also shown efficacy in models for analgesia (Xu X.-J., Hao J.-X, Seiger A., and Wiesenfeld-Hallin Z., J. Pharmacol. Exp. Ther., 1993;267:140), and epilepsy (Namba T., Morimoto K., Sato K., Yamada N., and Kuroda S., Brain Res., 1994;638:36; Brown S. E. and McCulloch J., Brain Res., 1994;641:10; Yamaguchi S. I., Donevan S. D., and Rogawski M. A., Epilepsy Res., 1993;15:179; Smith S. E., Durmuller N., and Meldrum B. S., Eur. J. Pharmacol., 1991;201:179). AMPA receptor antagonists have also demonstrated promise in chronic neurodegenerative disorders such as Parkinsonism (Klockgether T., Turski L., Honoré T., Zhang Z., Gash D. M., Kurlan R., and Greenamyre J. T., Ann. Neurol., 1993;34(4):585–593).

Excitatory amino acid receptor antagonists that block NMDA receptors are also recognized for usefulness in the treatment of disorders. NMDA receptors are intimately involved in the phenomenon of excitotoxicity, which may be a critical determinant of outcome of several neurological disorders. Disorders known to be responsive to blockade of the NMDA receptor include acute cerebral ischemia (stroke or cerebral trauma, for example), muscular spasm, convulsive disorders, neuropathic pain, and anxiety, and may be a significant causal factor in chronic neurodegenerative disorders such as Parkinson's Disease (Klockgether T. and Turski L., Ann. Neurol., 1993;34:585–593), human immunodeficiency virus (HIV) related neuronal injury, amyotrophic lateral sclerosis (ALS), Alzheimer's Disease (Francis P. T., Sims N. R., Procter A. W., and Bowen D. M., J. Neurochem., 1993;60(5):1589–1604), and Huntington's Disease. (See Lipton S., TINS, 1993;16(12):527–532; Lipton S. A. and Rosenberg P. A., New Eng. J. Med., 1994;330 (9):613–622; and Bigge C. F., Biochem. Pharmacol., 1993;45:1547–1561 and references cited therein.) NMDA receptor antagonists may also be used to prevent tolerance to opiate analgesia or to help control withdrawal symptoms from addictive drugs (Eur. Pat. Appl. 488,959A).

Copending U.S. Ser. No. 08/443,507 discloses glutamate receptor antagonist quinoxalinedione derivatives represented by the formula:

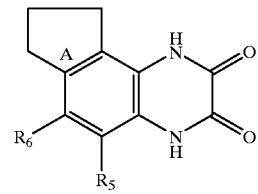

wherein A is a 5 to 7 atom containing ring having a nitrogen which may be substituted by hydrogen, alkyl, or $CH_2CH_2OH$. This application does not disclose or suggest compounds having the instant sulfonamides as substituents, or the requisite methodology to prepare the same.

Copending application U.S. Ser. No. 08/869,515 teaches glutamate receptor antagonists which are quinoxalinediones of formula

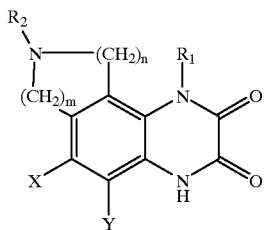

or a pharmaceutically acceptable salt thereof wherein $R_1$ is hydrogen, an alkyl, or an alkylaryl;

X and Y are independently hydrogen, halogen, nitro, cyano, trifluoromethyl, COOH, $CONR_4R_5$, $SO_2CF_3$, $SO_2R_4$, $SONR_4R_5$, alkyl, alkenyl, $(CH_2)_zCONR_4R_5$, $(CH_2)_zCOOR_4$, or $NHCOR_4$, wherein $R_4$ and $R_5$ are independently hydrogen, alkyl having 1 to 6 carbon atoms, cycloalkyl, or alkylaryl, and z is an integer from 0 to 4;

$R_2$ is $alkylCOOR_3$, alkylamine, alkylguanidine, aryl, alkylaryl, COalkyl, COalkylaryl, $CONR_3$alkyl, $CONR_3$aryl, $CONR_3$alkylaryl, $CSNR_3$alkyl, $CSNR_3$alkylaryl or a common amino acid moiety joined by an amide bond, wherein $R_3$ is hydrogen, alkyl, or alkylaryl; and m and n are independently 0, 1, or 2 provided that m+n is >1.

This application does not disclose or suggest the compounds of the instant invention having sulfonamides as substituents at the a- or b-positions nor the methodology to prepare them.

JP06228112-A discloses glutamate receptor antagonists which are quinoxaline-2,3(1 H,4H)-dione derivatives of formula

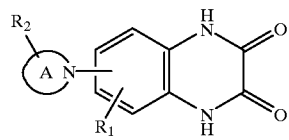

wherein $R_1$ is H, $NO_2$, or $CF_3$;

Ring A is a nitrogen-containing saturated heterocyclic group which may contain sulfur or oxygen;

$R_2$ is H, OH, lower alkoxy, COOH, lower alkoxy carbonyl, $NH_2$, or lower alkoxy carbonyl-amino. This reference does not teach or suggest the instant compounds which must be attached to the quinoxaline dione fused ring system by an alkylene.

WO 93/08188 covers a tricyclic quinoxalinedione of formula

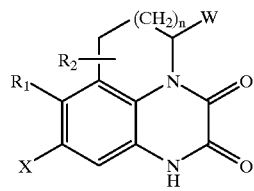

as useful or selective antagonists of glutamate receptors.

European Patent Application 0627434 covers tricyclic quinoxalinedione of Formula I below which are selective antagonists of glycine binding site of the NMDA receptor

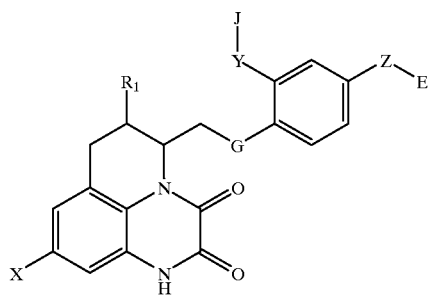

wherein

X represents hydrogen, alkyl, halogen, cyano, trifluoromethyl, or nitro;

$R_1$ represents hydrogen, alkyl, cycloalkyl, or cycloalkylalkyl;

G represents —$CONR_2$ or —$NR_2CO$—, wherein $R_2$ represents hydrogen or alkyl J represents an acidic group or a group which is convertible thereto in vivo;

E represents a basic group or a group which is convertible thereto in vivo;

Y represents a single bond, alkylene, alkenylene, substituted alkylene, or $Y_1$—Q—$Y_2$, wherein $Y_1$ represents a single bond or alkylene, $Y_2$ represents alkylene, and Q represents a heteroatom selected from oxygen or sulfur; and Z represents alkylene.

WO 94/26747 discloses compounds of Formula I below as useful in the treatment of cerebrovascular disorder

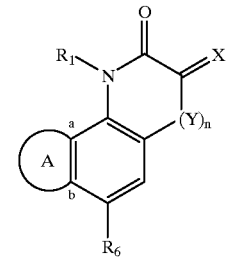

wherein $R_1$ is hydrogen, alkyl, or benzyl;

X is 0 or $NOR_2$, wherein $R_2$ is hydrogen, alkyl, or benzyl;

Y is N—$R_4$, wherein $R_4$ is hydrogen, OH, or alkyl;

n is 0 or 1;

$R_6$ is phenyl, naphthyl, thienyl, pyridyl, all of which may be substituted one or more times with substituents selected from the group consisting of halogen;

$CF_3$, $NO_2$, amino, alkyl, alkoxy, and phenyl; and

A is a ring of 5 to 7 atoms fused with the benzo ring at the positions marked a and b.

The compounds of the instant invention differ from the art in that they provide noncoplanar compounds with greater solubility and, therefore, better ability to penetrate the blood-brain barrier. These are important attributes in pharmaceuticals.

An object of this invention is to provide novel quinoxalinediones with sulfonamides at the a- or b-positions which function as antagonists.

SUMMARY OF THE INVENTION

The present invention pertains to compounds represented by Formula I:

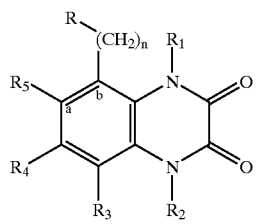

or a pharmaceutically acceptable salt thereof wherein R, $R_1$, $R_2$, $R_3$, $R_4$, $R_5$, and n are as described below.

The present invention also pertains to a pharmaceutical composition containing the compound defined by Formula I in an amount effective to treat cerebrovascular disorders responsive to the blockade of glutamate receptors (such as the α-amino-3-hydroxy-5-methyl-4-isoxazole propionic acid (AMPA) receptor and the kainate receptor), and a pharmaceutically acceptable carrier. Exemplary disorders responsive to such treatment include cerebral ischemia caused by cerebral trauma, stroke, hypoglycemia, heart attack, and surgery; anxiety and schizophrenia; and chronic neurodegenerative disorders such as Huntington's Disease, ALS, Parkinsonism, and Alzheimer's Disease. The pharmaceutical composition of this invention may also be employed as an analgesic or the treatment of epilepsy.

The invention further relates to a method of treating cerebrovascular disorders responsive to the antagonism of glutamate or aspartate receptors in a human by administering a pharmaceutically effective amount of the 2,3-quinoxalinediones of this invention and further to administering said compound in a unit dosage form.

The invention further relates to novel methods of preparing the 2,3-quinoxalinediones and to novel intermediates useful in their preparation.

DETAILED DESCRIPTION OF THE INVENTION

The substituted quinoxaline-2,3-diones of the instant invention are those of Formula I

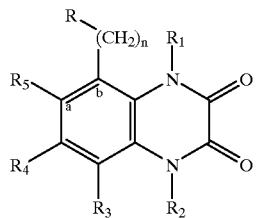

or a pharmaceutically acceptable salt thereof wherein

R is a sulfonamide;

n is an integer of from 1 to 4;

$R_1$ is hydrogen, alkyl, aralkyl, carboxyalkyl, phosphoroalkyl, or phosphonoalkyl;

$R_2$ is hydrogen, hydroxy, or amino;

$R_3$ and $R_4$ are each independently hydrogen, alkyl, cycloalkyl, alkenyl, aryl, heteroaryl, halogen, haloalkyl, nitro, cyano, $SO_2CF_3$, $CH_2SO_2R_6$, $(CH_2)_m$ $CO_2R_6$, $(CH_2)_m CONR_7R_8$, $(CH_2)_m SO_2NR_7R_8$, or $NHCOR_6$ wherein m is an integer of from 0 to 4, and $R_6$, $R_7$, and $R_8$ are each independently selected from hydrogen, alkyl, cycloalkyl, haloalkyl, or aralkyl;

$R_5$ is hydrogen, alkyl, alkenyl, cycloalkyl, halogen, haloalkyl, aryl, aralkyl, heteroaryl, heteroaralkyl, nitro, cyano, $SO_2CF_3$, $(CH_2)_m CO_2R_9$, $(CH_2)_m CONR_9R_{10}$, $SONR_9R_{10}$, or $NHCOR_9$;

m is an integer of from 0 to 4;

$R_9$ and $R_{10}$ are each independently hydrogen, alkyl, cycloalkyl, haloalkyl, or aralkyl; and $R_5$ may be at the a-position and R—$(CH_2)_n$— at the b-position on the ring.

Preferred compounds are those of Formula I wherein R is a straight chain sulfonamide

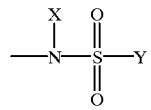

or sulfonamide in a mono- or bi-cyclic ring, unsubstituted or substituted by from 1 to 4 substituents, and is

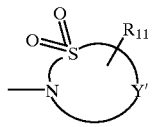

of from 4 to 7 atoms or

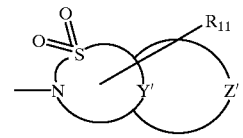

of from 8 to 12 atoms attached at N to the quinoxaline ring through —$(CH_2)_n$— at the a- or b-position, wherein $R_{11}$ is from 1 to 4 substituents independently selected from hydrogen, hydroxy, hydroxyalkyl, alkyl, alkoxy, alkoxyalkyl, —$NR_{12}R_{13}$, aminoalkyl, alkenyl, alkynyl, thiol, thioalkyl, alkylthioalkyl, aryl, aralkyl, heteroaryl, heteroaralkyl, heterocycloalkyl, cycloalkyl, $(CH_2)_n$ $(R_{14})$ $COR_{15}$; wherein $R_{12}$ and $R_{13}$ are independently selected from hydrogen, alkyl, cycloalkyl, heterocycloalkyl, aralkyl, and aryl; $R_{14}$ is hydrogen, alkyl, or aralkyl; $R_{15}$ is hydroxy, alkoxy, —$NR_{12}R_{13}$, or haloalkyl; or $R_{11}$ may be 2 substituents attached at the same carbon;

X is hydrogen, alkyl, aralkyl, aryl, heteroaryl, cycloalkyl, heterocycloalkyl, alkylaminoalkyl, hydroxy, hydroxyalkyl, and alkoxyalkyl;

Y, Y', and Z' are each independently carbon which is substituted by hydrogen, alkyl, alkoxyl, alkoxyalkyl, —$NR_{12}R_{13}$, aminoalkyl, aryl, aralkyl, heteroaryl, heteroaralkyl, cycloalkyl, carboxyalkyl, alkylaminoalkyl, heteroaryl, heterocycloalkyl, hydroxy, hydroxyalkyl, or is —O—, —S—, —SO—, —$SO_2$—, $NR_{16}$—, wherein $R_{16}$ is alkyl, hydrogen, aralkyl, heteroaralkyl, aryl, heteroaryl, cycloalkyl, heterocycloalkyl, —$C(O)OR_{17}$, —$C(O)R_{17}$, —$CH_2C(O)R_{18}$, —$CH_2C(O)NR_{19}R_{20}$ wherein R₁₇ is alkyl, aralkyl, cycloalkyl, heterocycloalkyl, aryl, or heteroaryl;

R₁₈ is alkyl, aralkyl, hydroxyl;

R₁₉ and R₂₀ are each independently hydrogen and alkyl.

Bicyclic structures encompassed in this invention include Spiro ring structures, wherein both ends of a second ring are attached to the same carbon unit on the parent ring.

For monocyclic and bicyclic structures wherein Y' and Z' represent a carbon atom, the structure may also include an integral double bond.

More preferred compounds of Formula I wherein R is a sulfonamide

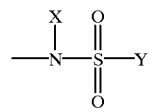

are those wherein

X is selected from hydrogen, alkyl, aralkyl, aryl, heteroaryl, cycloalkyl, heterocycloalkyl, and Y is selected from alkyl, aralkyl, heteroaralkyl, cycloalkyl, heterocycloalkyl, aryl, heteroaryl, alkoxy, alkoxyalkyl, alkylaminoalkyl, carboxyalkyl;

or is a side-chain amide such as —(CH)$_p$(R$_{21}$)C(O)NR$_{22}$R$_{23}$ wherein p is an integer of from 1 to 6, R$_{21}$ is hydrogen, alkyl, aralkyl, aryl, and R$_{22}$ and R$_{23}$ are each independently hydrogen, alkyl, aralkyl, aryl, heteroaryl, alkoxycarbonyl, aralkoxycarbonyl or joined together to form a saturated ring of from 5 to 7 members.

Still more preferred are those compounds of Formula I wherein R is a sulfonamide

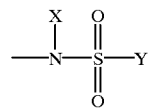

wherein

X is selected from methyl, ethyl, isopropyl, and butyl and

Y is selected from methyl, ethyl, isopropyl, propyl, butyl, benzyl, cyclopentyl, cyclohexyl, 2- or 3-pyrrolidinyl, 2- or 3-tetrahydro-furanyl, 2-, 3-, or 4-piperidinyl, substituted phenyl, 2- or 3-furanyl, 2- or 3-thienyl, 2- or 3-benzfuranyl, 2- or 3-benzthienyl, 2- or 3-indolyl, 2-benzimidazolyl, imidazolyl, 3- or 4-piperidinyl, phenyl, 2- or 3-indolyl, tetrazolyl, imidazolyl, pyrrazolyl, naphthyl, oxadiazolyl, and 2-benzimidazolyl.

More preferred compounds of Formula I wherein R is a sulfonamide in a mono- or bi-cyclic ring, unsubstituted or substituted by from 1 to 4 substituents, and is

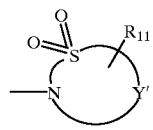

of from 4 to 7 atoms or

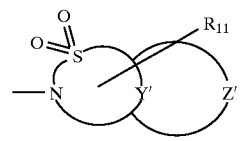

of from 8 to 12 atoms are those wherein R is a mono-cyclic ring of from 4 to 7 atoms and Y' is methylene, O, S, or N—R$_{25}$ wherein R$_{25}$ is H, alkyl, aryl.

The open chain sulfonamides are preferred over the mono- and bicyclic sulfonamides Most preferred compounds of Formula I are selected from:

N-Methyl-N-(6-methyl-7-nitro-2,3-dioxo-1,2,3,4-tetrahydro-quinoxalin-5-ylmethyl)-methanesulfonamide;

4,N-Dimethyl-N-(6-methyl-7-nitro-2,3-dioxo-1,2,3,4-tetrahydro-quinoxalin-5-ylmethyl)-benzenesulfonamide;

2,4,6-Triisopropyl-N-methyl-N-(6-methyl-7-nitro-2,3-dioxo-1,2,3,4-tetrahydro-quinoxalin-5-ylmethyl)-benzene sufonamide; and, Naphthalene-2-sulfonic acid methyl-(6-methyl-7-nitro-2,3-dioxo-1,2,3,4-tetrahydro-quinoxalin-5-ylmethyl)-amide.

Some of the compounds of Formula I are capable of further forming both pharmaceutically acceptable acid addition and/or base salts. These forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, isethionate, and the like. Also contemplated are salts of amino acids such as arginate and the like and gluconate, galacturonate (see, for example, Berge S. M., et al., "Pharmaceutical Salts," *Journal of Pharmaceutical Science*, 1977;66:1–19).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention may exist as a mixture of cis and trans isomers or as the individual cis and trans isomers or R and S stereoisomers. The mixture of isomers as well as the individual isomers are intended to be encompassed within the scope of the present invention.

In the compounds of Formula I, the term "alkyl" means a straight or branched hydrocarbon radical having from 1 to 6 carbon atoms and includes, for example, methyl, ethyl, n-propyl, isopropyl, n-butyl, sec-butyl, isobutyl, tert-butyl, n-pentyl, n-hexyl, and the like.

The term "carboxyalkyl" means alkyl as above and attached to a carboxy group.

The term "phosphoroalkyl" means alkyl as above and attached to a phosphoro group.

The term "phosphonoalkyl" means alkyl as above and attached to a phosphono group.

The term "alkenyl" means a straight or branched unsaturated hydrocarbon radical having from 3 to 6 carbon atoms and includes, for example, 2-propenyl, 1-butenyl, 2-butenyl, 1-pentenyl, 2-pentenyl, 3-methyl-3-butenyl, 1-hexenyl, 2-hexenyl, 3-hexenyl, and the like.

Alkynyl means a straight or branched unsaturated hydrocarbon radical of from 2 to 6 carbon atoms and includes but is not limited to ethynyl, 2,3-propynyl, 1,2-propynyl, and 3,4-butynyl.

"Alkoxy" is O-alkyl of from 1 to 6 carbon atoms as defined above for "alkyl."

The term "aryl" means an aromatic radical which is a phenyl group, a phenyl group substituted by 1 to 4 substituents selected from alkyl as defined above, alkoxy as defined above, thioalkoxy as defined above, hydroxy, halogen, trifluoromethyl, amino, alkylamino as defined above for alkyl, dialkylamino as defined for alkyl, or 1,3-benzodioxol-5-yl.

The term "aralkyl" means aryl and alkyl as defined above and includes but is not limited to benzyl, 2-phenylethyl, and 3-phenylpropyl; a preferred group is phenyl.

The term "heteroaryl" means a heteroaromatic radical which is 2-, 3-, or 4-pyridinyl, 2-, 4-, or 5-pyrimidinyl, 2- or 3-thienyl, isoquinolines, quinolines, imidazolines, pyrroles, indoles, and thiazoles.

"Halogen" is fluorine, chlorine, bromine, or iodine.

The term "haloalkyl" means halogen and alkyl as defined above, for example, but not limited to, trifluoromethyl and trichloromethyl.

"Alkylaryl" means aryl as defined above and alkyl as defined above, for example, but not limited to benzyl, 2-phenylethyl, 3-phenylpropyl; a preferred group is benzyl.

The term "heterocycloalkyl" means a nonaromatic ring with from 4 to 7 members, with up to 4 heteroatoms for example, N, O, and S.

Common amino acid moiety means the naturally occurring α-amino acids, unnatural amino acids, substituted β, γ, δ amino acids and their enantiomers.

Common amino acids are: Alanine, β-alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

Modified and unusual amino acids are as would occur to a skilled chemist and are, for example, but not limited to:

10,11-Dihydro-5H-dibenzo[a,d]cyclohepten-5-yl)glycine or α-Amino-10,11-dihydro-5H-dibenzo[a,d]cycloheptene-5-acetic acid (Paraphenyl)phenylalanine,
3,3-Diphenylalanine,
3-Hydroxyproline,
4-Hydroxyproline,
N-Methylphenylalanine,
N-Methylaspartic acid,
N-Methylisoleucine,
N-Methylvaline,
Norvaline,
Norleucine,
Ornithine,
2-Aminobutyric acid,
2-Amino-4-pentanoic acid (Allylglycine),
$N^G$-Nitroarginine,
2-Amino-3-(2-amino-5-thiazole)propanoic acid,
2-Amino-3-cyclopropanepropanoic acid (Cyclopropylalanine),
Cyclohexylalanine (Hexahydrophenylalanine),
N-Methylcyclohexylalanine (N-Methylhexahydrophenylalanine),
2-Amino-4,4(RS)-epoxy-4-pentanoic acid,
$N^{im}$-2,4-Dinitrophenylhistidine,
2-Aminoadipic acid,
2-Amino-5-phenylpentanoic acid (Homophenyl-alanine),
Methionine sulfoxide,
Methionine sulfone,
3-(1'-Naphthyl)alanine,
3-(2'-Naphthyl)alanine,
2-Amino-3-cyanopropanoic acid (Cyanoalanine),
Phenylglycine,
2-Aminopentanoic acid (Propylglycine),
2-Amino-6-(1-pyrrollo)-hexanoic acid,
2-Amino-3-(3-pyridyl)-propanoic acid (3-Pyridylalanine),
1,2,3,4-Tetrahydro-3-isoquinolinecarboxylic acid,
2-Amino-3-(4-thiazolyl)-propanoic acid,
O-Tertiary butyl-tyrosine,
O-Methyl-tyrosine,
O-Ethyl-tyrosine,
$N^{in}$-Formyl-tryptophan,
5H-Dibenzo[a,d]cycloheptene glycine,
9H-Thioxanthene glycine, and
9H-Xanthene glycine.

Spiro rings include but are not limited to 5- to 7-membered carbocyclic or heterocyclic ring with up to 4 heteroatoms.

The compounds of the invention exhibit valuable biological properties because of their strong excitatory amino acid (EAA) antagonizing properties at one of several binding sites on glutamate receptors: the AMPA ((RS)-amino-3-hydroxy-5-methyl-4-isoxazolepropionic acid (or kainic acid) binding site on AMPA (non-NMDA) receptors or the glycine site of NMDA receptors.

The compounds of the present invention exhibit binding affinity for the AMPA receptors measured as described in Honoré T., et al., *Neuroscience Letters*, 1985;54:27–32. Preferred compounds demonstrate $IC_{50}$ values <100 μM in this assay. The compounds of the present invention exhibit binding affinity for the kainate site (non-NMDA receptor) measured as described in London E. D. and Coyle J., *Mol. Pharmacol.*, 1979; 15:492. The compounds of the present invention exhibit binding affinity for the glycine site of the NMDA receptor measured as described in Jones S. M., et al., *Pharmacol. Methods*, 1989;21:161. To measure functional AMPA antagonist activity, the effects of the agent on AMPA-induced neuronal damage in primary cortical neuronal cultures was examined using techniques similar to those outlined by Koh J.-Y., et al., *J. Neurosci.*, 1990;10:693. In addition, the neuronal damage produced by long-term exposure to 100 μM AMPA may be measured by the release of the cytosolic enzyme lactate dehydrogenase (LDH).

Selected compounds of the present invention were tested by one or more of the above-described assays. The data obtained in the assays is set forth in Table 1 below. The $IC_{50}$ values are a measure of the concentration (μM) of the test substance which inhibits 50% of an induced release from the tested receptors.

TABLE 1

Quinoxaline 2,3-diones

| Compound | $IC_{50}$(μM) | | |
|---|---|---|---|
| | AMPA | KA | GLY |
| 1. N-Methyl-N-(6-methyl-7-nitro-2,3-dioxo-1,2,3,4-tetrahydro-quinoxalin-5-ylmethyl)-methanesulfonamide | 0.21 | 0.29 | 0.1 |
| 2. 4,N-Dimethyl-N-(6-methyl-7-nitro-2,3-dioxo-1,2,3,4-tetrahydro-quinoxalin-5-ylmethyl)-benzensulfonamide | 0.56 | 2.63 | >1 |
| 3. 2,4,6-Triisopropyl-N-methyl-N-(6-methyl-7-nitro-2,3-dioxo-1,2,3,4-tetrahydro-quinoxalin-5-ylmethyl)-benzenesulfonamide | 2.6 | 4.77 | >1 |
| 4. Naphthalene-2-sulfonic acid methyl-(6-methyl-7-nitro-2,3-dioxo-1,2,3,4-tetrahydro-quinoxalin-5-ylmethyl)-amide | 18.0 | 26.0 | >1 |

Additionally, as a preliminary indicator of in vivo CNS activity related to anticonvulsant activity and potential neuroprotection, a maximal electroshock assay in CF-1 strain mice (20–25 g) was performed with corneal electrodes by conventional methods as described previously (Krall, et al., *Epilepsia*, 1988;19:409–428). The compounds of this invention generally demonstrated $ED_{50}$ values of <50 mg/kg.

The compounds of the invention, together with a conventional adjuvant, carrier, or diluent, may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Tablets containing 10 mg of active ingredients or, more broadly, 0.1 to 100 mg per tablet, and accordingly suitable representative unit dosage forms.

Solid forms of pharmaceutical compositions for PO administration and injectable solutions are preferred.

The compounds of this invention are extremely useful in the treatment of central nervous system disorders related to their biological activity. The compounds of this invention may accordingly be administered to a subject, including a human, in need of treatment, alleviation, or elimination of an indication associated with the biological activity of the compounds. This includes especially excitatory amino-acid-dependent psychosis, excitatory amino-acid-dependent anoxia, excitatory amino-acid-dependent ischemia, excitatory amino-acid-dependent Parkinsonism, excitatory amino-acid-dependent convulsions, and excitatory amino-acid-dependent migraine. Suitable dosage ranges are 0.1 to 1000 mg daily, 10 to 50 mg daily, and especially 30 to 100 mg daily, dependent as usual upon the exact mode of administration, form in which administered, the indication toward which the administration is directed, the subject involved, and the body weight of the subject involved, and further, the preference and experience of the physician or veterinarian in charge.

The schemes and examples which follow are intended as an illustration of certain preferred embodiments of the invention, and no limitation of the invention is implied.

General Scheme I

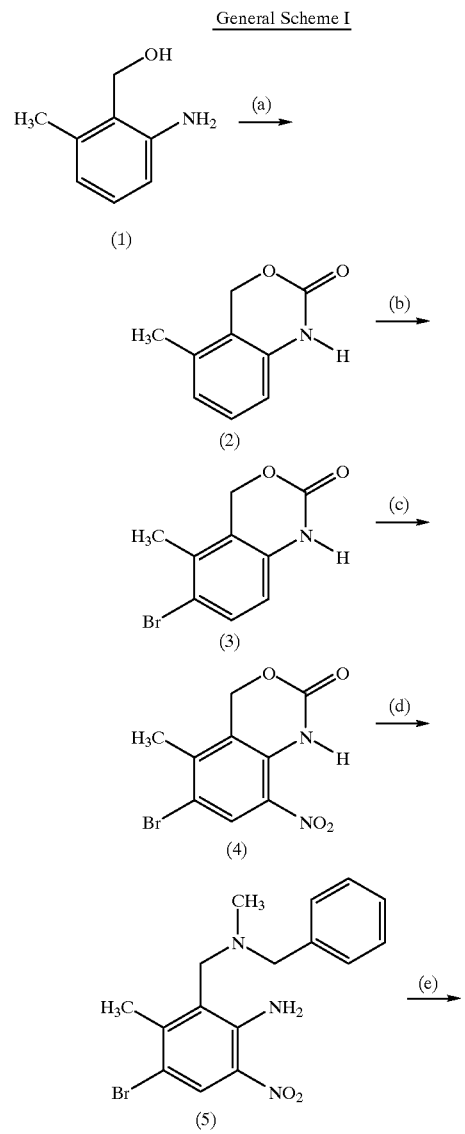

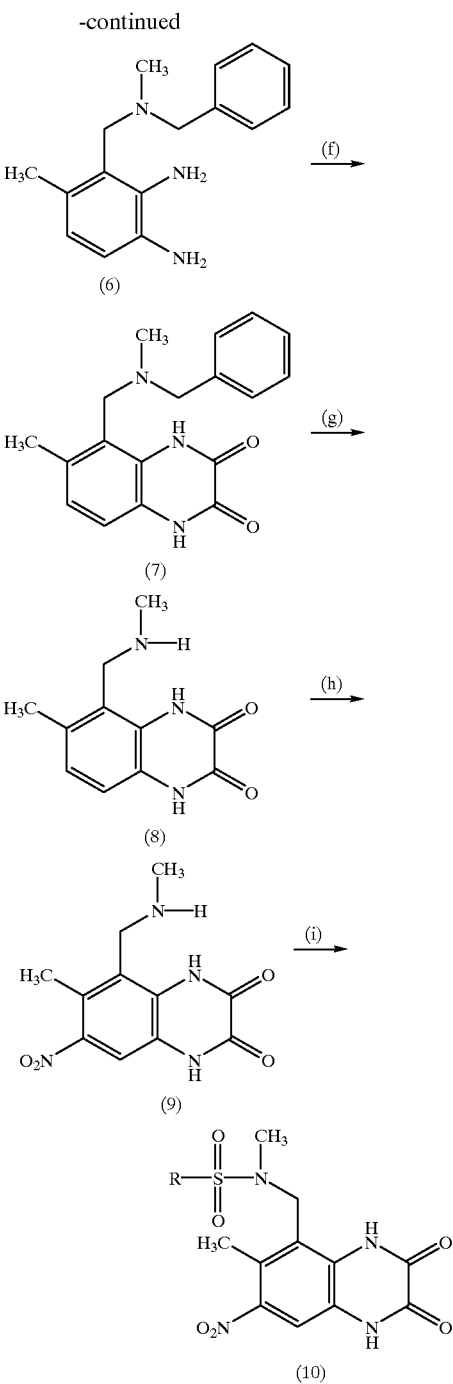

Step (a) of Scheme I above involves formation of a cyclic carbamate derivative of Formula (2) by reacting aminobenzyl alcohol derivative of Formula (1) with a reactive acylating agent, preferably phosgene in the presence of a tertiary organic base like triethylamine in a ethereal solvent, preferably THF at temperatures ranging from −10° C. to room temperature. Alternatively, aqueous inorganic bases such as sodium carbonate, sodium bicarbonate, or potassium carbonate, preferably aqueous sodium carbonate. The reaction mixture is stirred for 2 to 16 hours and diluted with water. Product is extracted with water insoluble solvent like ethyl acetate. The extracts washed with water and brine and dried over $MgSO_4$. The product was crystallized from solvent mixture, preferably EtOAc and pet. ether.

Step (b) involves bromination of the cyclic carbamate derivative of Formula (2) with a brominating agent like bromine in an acidic solvent mixture like AcOH and TFA. The reaction is done at temperatures between 10° C. to room temperature. Reaction mixture is stirred for around 2 hours and poured over ice water. The precipitate is filtered and dried at elevated temperatures, preferably at 120° C.

Step (c) involves the nitration of the bromo cyclic carbamate derivative as shown in Formula (3) with a nitrating agent like nitronium tetrafluoroborate, nitric acid or potassium nitrate, preferably potassium nitrate in an acidic solvent like sulfuric acid at temperatures between 0° C. to room temperature. Reaction carried out for 4 to 16 hours, preferably around 14 hours and poured over ice. The precipitate was filtered and air dried to give the desired product.

Step (d) involves the reaction of the nitro cyclic carbamate derivative as shown in Formula (4) with a secondary amine, preferably N-methyl-benzylamine. Reaction is carried out at elevated temperatures between 100° C. to 180° C. with or without a solvent like N-methyl-formamide, preferably without a solvent for about 18 hours. Volatile materials were evaporated under reduced pressure and the product isolated from the crude via column chromatography using pet. ether:EtOAc as the solvent mixture or crystallization to give the desired benzylamine derivative.

Step (e) involves the hydrogenation ($H_2$, around 50 psi) of the benzylamine derivative as shown in Formula (5) in the presence of a catalyst like Ra Ni and a base, preferably KOH in a hydroxylated solvent like methanol. The catalyst is filtered off, and the filtrate is evaporated to give the o-phenylene diamine derivative, which is used in the next step without additional purification.

Step (f) involves cyclization reaction from quinoxaline 2,3-dione derivative by reacting the o-phenylene diamine derivative as shown in Formula (6) with an oxalic acid derivative such as dimethyl oxalate in a hydroxylated or ethereal solvent, preferably THF at reflux temperature. Reaction carried out for about 12 to 24 hours, preferably 16 hours and partially evaporated to give a crude product which is purified by crystallization.

Step (g) involves reductive cleavage of the benzyl group of the N-methylbenzyl-amine side-chain in compound shown in Formula (7). The reductive in cleavage is carried out via hydrogenation ($H_2$, 50 psi) of the benzylamine quinoxaline 2,3-dione intermediate as shown in Formula (7) using Pd/C (5–20%), preferably Pd/C (20%) as a catalyst in a polar solvent like DMF. The suspension was filtered, and the filtrate was evaporated to give a solid, which was crystallized from a hydroxylated solvent like methanol.

Step (h) involves nitration of the quinoxaline 2,3-dione derivative shown in Formula (8) using potassium nitrate or nitric acid, preferably potassium nitrate as the nitrating agent. The reaction is carried out in an acidic solvent such as sulfuric acid from temperatures ranging from 0° C. to room temperature. Reaction mixture is poured in ice, and the precipitate obtained is filtered and air dried.

Step (i) involves reaction of the N-methyl-benzylamine moiety of quinoxaline-2,3-dione shown in Formula (9) with various sulfonyl chlorides to give the corresponding sulfonamide. Thus, a solution of Compound 9 in a polar solvent like DMF is treated with 0.95 to 1.5 equivalents of sulfonyl chloride at temperatures ranging from 0° C. to room temperatures preferably room temperature. The reaction is carried out from 2 to 18 hours depending on the electrophile preferably around 16 hours. Reaction mixture is evaporated to dryness, and the residue is treated with water for 0.5 hour and filtered. The desired sulfonamide was purified by crystallization ($CHCl_3$ and $CH_3OH$ mixture) or chromatography ($SiO_2$) using $CHCl_3$:MeOH mixture as the eluent.

These general experimental schemes cover most of the final products of the invention. Others are made by known experimental procedures.

The above methodology can be used to synthesize sulfonamides of the invention as follows:

SCHEME 1

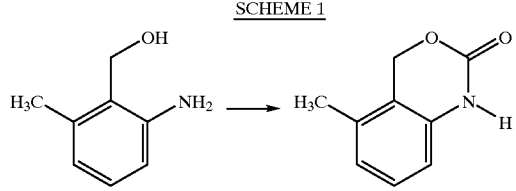

5-Methyl-1,4-dihydro-benzo[d][1,3]-oxazin-2-one

To a solution of (2-amino-6-methyl-phenyl)-methanol (2.74 g, 20 mmol) and triethylamine (4.04 g, 40 mmol) in THF (150 mL), phosgene (12.5% solution in toluene, 17.42 g, 22 mmol) was added dropwise at 0° C. Reaction mixture was allowed to warm to room temperature and stirred for 16 hours. Water (150 mL) was added under stirring, followed by EtOAc (2×100 mL). EtOAc extracts were washed with water and brine and dried over $MgSO_4$. The product (buff solid) was crystallized from EtOAc:pet. ether mixture. (Yield: 2.37=73%); mp 222–226° C.; MS (CI): M+1=163.

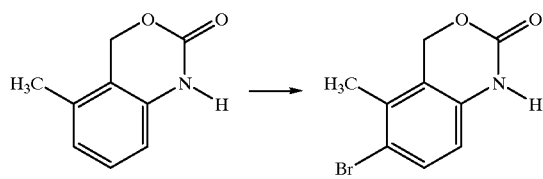

6-Bromo-5-methyl-1,4-dihydro-benzo[d][1,3]oxazine-2-one

To a solution of 5-methyl-1,4-dihydro-benzo[d][1,3] oxazin-2-one (0.695 g, 4.3 mmol) in acetic acid (5 mL), $Br_2$ (0.805 g=5 mmol) solution in TFA (5 mL)+acetic acid (5 mL) was added at 10° C. Reaction mixture was stirred for 2 hours and poured over ice water. Yellow precipitate was filtered and dried at 120° C. (Yield: 0.941 g=90%); MS (CI): M+1=243; M+2=244.

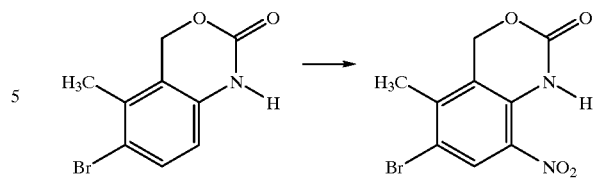

6-Bromo-5-methyl-8-nitro-1,4-dihydro-benzo[d][1,3] oxazin-2-one

To a solution of 6-bromo-5-methyl-1,4-dihydro-benzo[d] [1,3]oxazin-2-one (0.726 g, 3 mmol) in concentrate $H_2SO_4$ (4 mL), $KNO_3$ (0.303 g, 3 mmol) was added at 0° C. Reaction mixture stirred 14 hours and poured over crushed ice. Yellow precipitate was obtained, which was filtered and dried. (Yield: 0.782=91%); MS (CI): M+1=288; M+2=289.

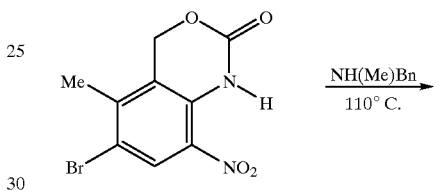

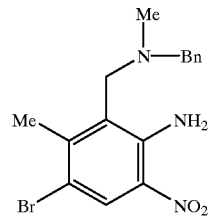

2-[(Benzyl-methyl-amino)-methyl]-4-bromo-3-methyl-6-nitro-phenylamine

6-Bromo-5-methyl-8-nitro-1,4-dihydro-benzo[d][1,3] oxazine-2-one (11.48 g, 40 mmol) was heated to 140° C. for 18 hours. TLC ($SiO_2$, pet. ether:EtOAc, 1:1) indicated completion. Volatile material concentrated on rotavap and the dark oil extracted with ethyl acetate (2×250 mL). Solvent evaporated to give viscous oil, which on trituration with ethyl acetate (150 mL) gave yellow crystalline product. Yield in two crops: 10.17 g=70%; MS (CI): M+1=364; Elemental analysis calculated for $C_{16}H_{18}BrN_3O_2$: C, 52.76; H, 4.98; N, 11.54. Found: C, 52.22; H, 4.87; N, 11.11.

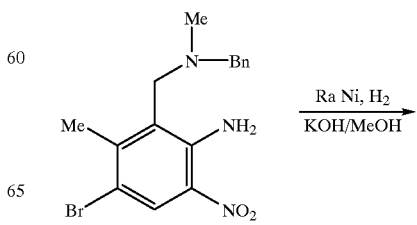

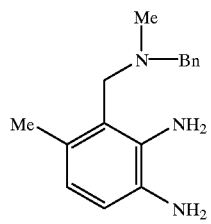

3-[(Benzyl-methyl-amino)-methyl]-4-methyl-benzene-1,2-diamine

2-[(Benzyl-methyl-amino)-methyl]-4-bromo-3-methyl-6-nitro-phenylamine (6 g, 16.5 mmol) was hydrogenated (Ra Ni, 3 g) in the presence of KOH (0.498 N). Reaction mixture filtered and extracted in CHCl$_3$ (200 mL) and washed with water and dried (MgSO$_4$). Solvent evaporated to give a dark oil 4.19 g=99%. H-NMR: 1.96 (s, 3H), 2.08 (s, 3H), 3.36–3.39 (m, 4H), 4.23 (s, 2H), 4.73 (s, 2H), 6.18 (d, 1H, J=7.3 Hz), 6.33 (d, 1H, J=7.3 Hz), 7.21–7.26 (m, 5H).

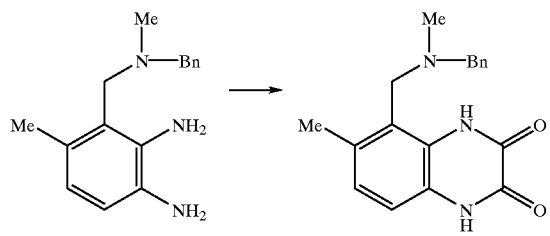

5-[(Benzyl-methyl-amino)-methyl]-6-methyl-1,4-dihydro-quinoxaline-2,3-dione

To a solution of diamine (4.19 g) in THF, dimethyl oxalate (2.36 g, 20 mmol) was added. Reaction mixture stirred at reflux for 16 hours and cooled. Buff ppt was filtered (2.93 g). Mother liquor gave two additional crops. Total yield: 3.945 g=77.4%; mp 205–206° C.; MS (CI): M+1=310.

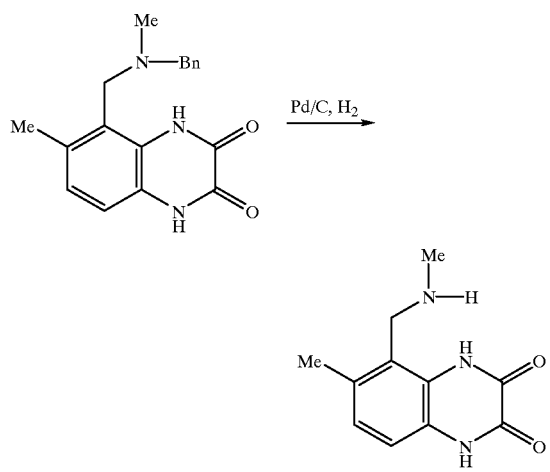

6-Methyl-5-methylaminomethyl-1,4-dihydro-quinoxaline-2,3-dione

A solution of 5-[(benzyl-methyl-amino)-methyl]-6-methyl-1,4-dihydro-quinoxaline-2,3-dione (3.23 g, 10.45 mmol) in DMF (100 mL) was hydrogenated (Pd/C, 20%, 0.5 g) in DMF (100 mL). The suspension was filtered, and the filtrate was evaporated to give a solid, which was crystallized from methanol. Yield: 1.276 g=56%. MS (CI): M+1=220.

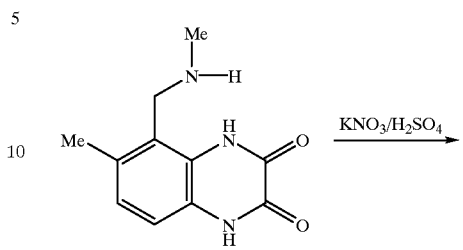

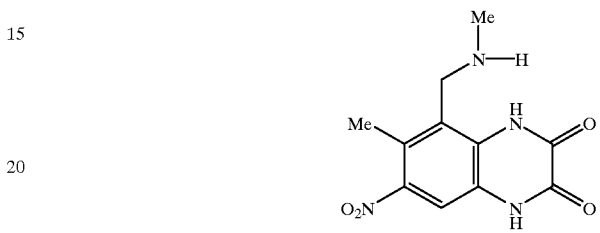

6-Methyl-5-methylaminomethyl-7-nitro-1,4-dihydro-quinoxaline-2,3-dione

To a cooled (10° C.) solution of 6-methyl-5-methylaminomethyl-1,4-dihydro-quinoxaline-2,3-dione (10° C.) of (1.23 g, 5.6 mmol) in concentrate H$_2$SO$_4$ (5 mL), KNO$_3$ (0.606 g, 6 mmol) was added. Reaction mixture stirred overnight and quenched with ice. Green ppt filtered and washed with ice-cold water and dried (0.77 g, 42%); mp 260–261° C. MS (CI): M+1=265.

General method for the synthesis of N-methyl sulfonamides

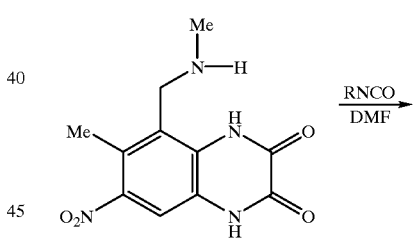

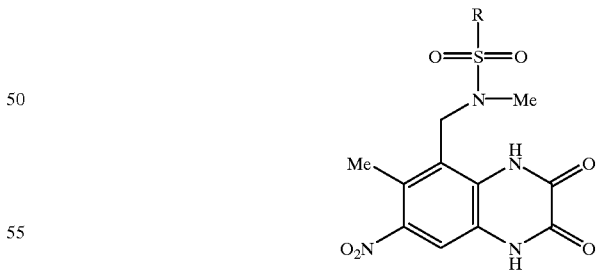

To a solution of 6-methyl-5-methylaminomethyl-7-nitro-1,4-dihydro-quinoxaline-2,3-dione (0.1 mmol) in DMF (2 mL), appropriate sulfonyl chloride (0.11 mmol) was added. Reaction mixture was stirred for 16 hours and evaporated. The residue was treated with water for 0.5 hour and filtered. The product was further washed with water (3×5 mL) and dried. The final product was purified by crystallization (CHCl$_3$/CH$_3$OH) mixture.

TABLE 2

Sulfonamide Derivatives of Quinoxaline 2,3-dione

| Compound | Structure | Yield % | MS (M + 1) |
| --- | --- | --- | --- |
| 1. N-Methyl-N-(6-methyl-7-nitro-2,3-dioxo-1,2,3,4-tetrahydro-quinoxalin-5-ylmethyl)-methanesulfonamide | 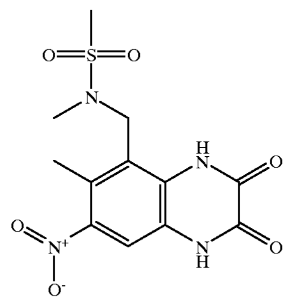 | 44 | 343 |
| 2. 4,N-Dimethyl-N-(6-methyl-7-nitro-2,3-dioxo-1,2,3,4-tetrahydro-quinoxalin-5-ylmethyl)-benzenesulfonamide | 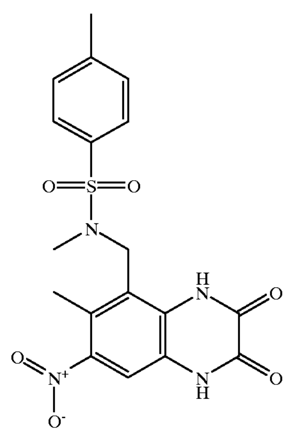 | 22 | 419 |
| 3. 2,4,6-Triisopropyl-N-methyl-N-(6-methyl-7-nitro-2,3-dioxo-1,2,3,4-tetrahydro-quinoxalin-5-ylmethyl)-benzenesulfonamide | 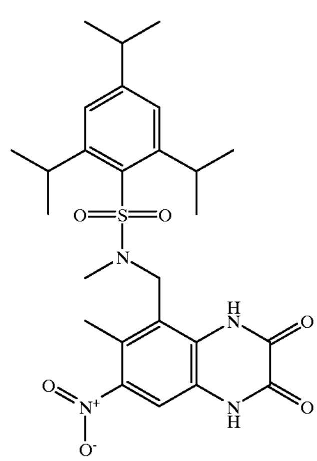 | 31 | 531 |

TABLE 2-continued

Sulfonamide Derivatives of Quinoxaline 2,3-dione

| Compound | Structure | Yield % | MS (M + 1) |
|---|---|---|---|
| 4. Naphthalene-2-sulfonic acid methyl-(6-methyl-7-nitro-2,3-dioxo-1,2,3,4-tetrahydro-quinoxalin-5-ylmethyl)-amide | 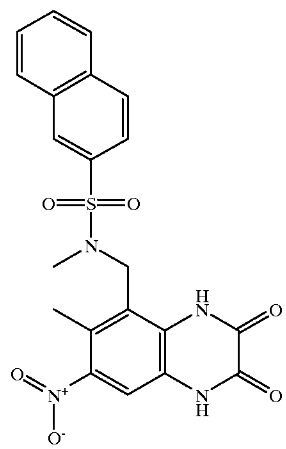 | 23 | 455 |

We claim:

1. A compound selected from the group consisting of:

N-Methyl-N-(6-methyl-7-nitro-2,3-dioxo-1,2,3,4-tetrahydro-quinoxalin-5-ylmethyl)-methanesulfonamide;

4,N-Dimethyl-N-(6-methyl-7-nitro-2,3-dioxo-1,2,3,4-tetrahydro-quinoxalin-5-ylmethyl)-benzenesulfonamide and 2,4,6-Triisopropyl-N-methyl-N-(6-methyl-7-nitro-2,3-dioxo-1,2,3,4-tetrahydro-quinoxalin-5-ylmethyl)-benzenesulfonamide.

2. A pharmaceutical composition comprising a therapeutically effective amount of a compound according to claim 1 together with a pharmaceutically acceptable carrier in unit dosage form.

3. A method for treating convulsions which comprises administering a therapeutically effective amount of a compound according to claim 1 to a patient in need of said treatment.

* * * * *